(12) United States Patent
Boland et al.

(10) Patent No.: US 6,253,404 B1
(45) Date of Patent: Jul. 3, 2001

(54) ELECTRICALLY OPERATED TOOTH-CLEANING DEVICE

(75) Inventors: Bernhard Boland, Frankfurt; Michael Stolper, Eschborn, both of (DE)

(73) Assignee: Braun GmbH, Kronberg (DE)

( * ) Notice: Subject to any disclaimer, the term of this patent is extended or adjusted under 35 U.S.C. 154(b) by 0 days.

(21) Appl. No.: 09/063,561

(22) Filed: Apr. 21, 1998

Related U.S. Application Data

(60) Provisional application No. 60/044,148, filed on Apr. 22, 1997.

(51) Int. Cl.[7] .................................... A46B 13/00
(52) U.S. Cl. .................. 15/22.1; 15/23; 15/24; 15/28; 15/29; 15/167.1; 132/308; 132/311; 132/322; 433/124; 433/216
(58) Field of Search ................ 15/22.1, 23, 24, 15/28, 29, 167.1; 433/125, 216; 132/322, 308, 311

(56) References Cited

U.S. PATENT DOCUMENTS

| | | | |
|---|---|---|---|
| 3,240,077 | * 3/1966 | Smith | 74/43 |
| 3,720,975 | * 3/1973 | Nelson | 15/167.1 |
| 3,939,520 | 2/1976 | Axelsson | 15/167.1 |
| 4,603,448 | * 8/1986 | Middleton et al. | 15/22.1 |
| 4,827,550 | * 5/1989 | Graham et al. | 15/28 |
| 5,148,568 | 9/1992 | Bojar et al. | 15/28 |
| 5,224,500 | 7/1993 | Stella | 132/322 |
| 5,383,242 | * 1/1995 | Bigler et al. | 15/22.1 |
| 5,700,146 | * 12/1997 | Kucar | 132/322 |
| 5,781,955 | * 7/1998 | Hendricks | 15/22.1 |
| 5,836,030 | * 11/1998 | Hazeu et al. | 15/28 |
| 5,851,116 | * 12/1998 | Margolis | 433/216 |

FOREIGN PATENT DOCUMENTS

| | | |
|---|---|---|
| 2 526 282 | 11/1983 | (FR) . |
| 81/03604 | * 12/1981 | (WO) ................ 15/22.1 |
| 92/18063 | 10/1992 | (WO) . |
| 94/04093 | 3/1994 | (WO) . |
| 96/32903 | * 10/1996 | (WO) . |

* cited by examiner

Primary Examiner—Krisanne Thornton
Assistant Examiner—Theresa T. Snider
(74) Attorney, Agent, or Firm—Fish & Richardson P.C.

(57) ABSTRACT

An electrically operated tooth-cleaning device being provided with a handle part having an electric drive motor. A hanle part can be connected with an attachment provided with a cleansing tool, with the cleaning tool being capable of being caused to rotate by the drive motor. A first cleaning tool of a first attachment is capable of being connected directly with the drive motor, and cleaning tool of a second attachment can be couple trough a transmission with the drive motor.

71 Claims, 9 Drawing Sheets

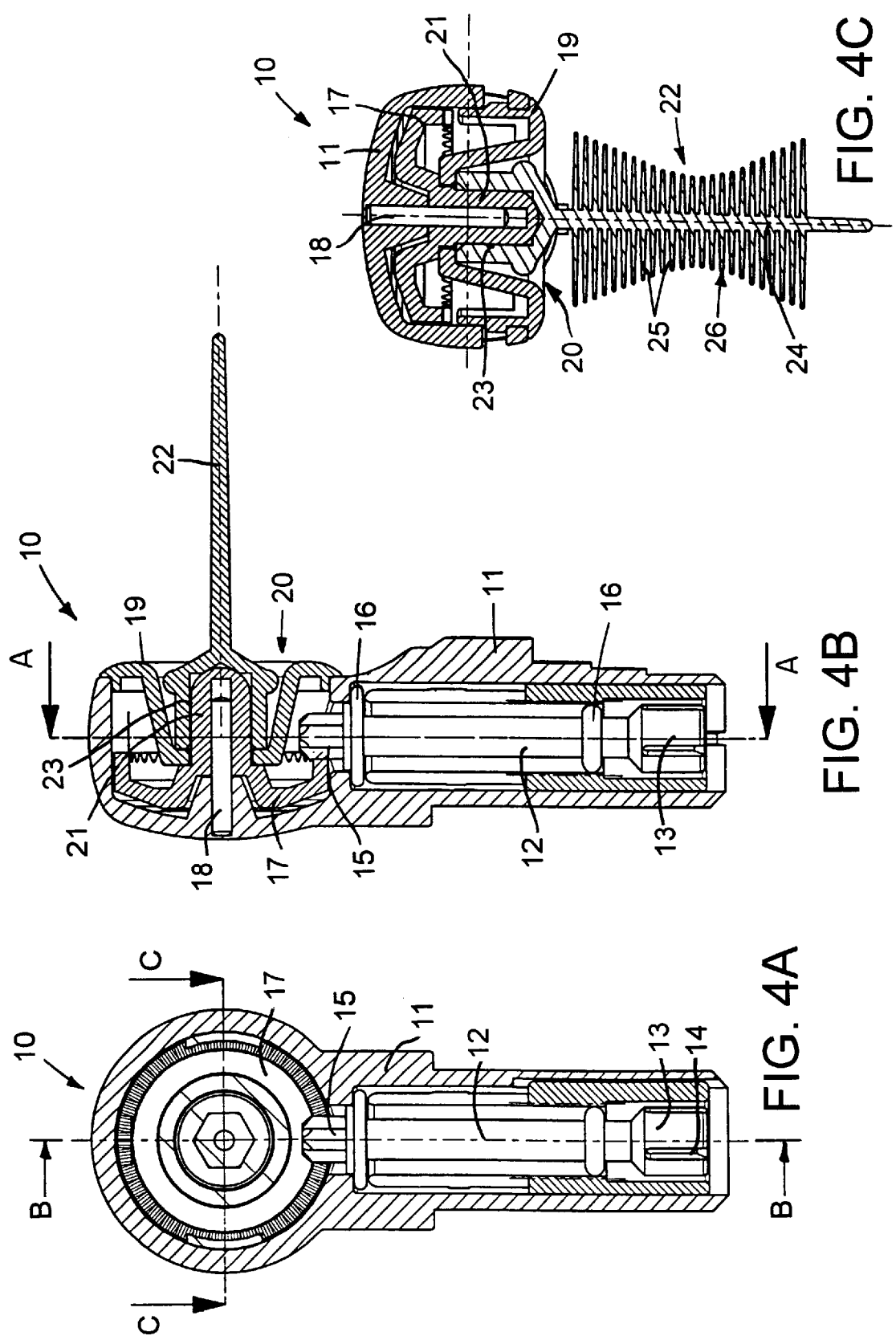

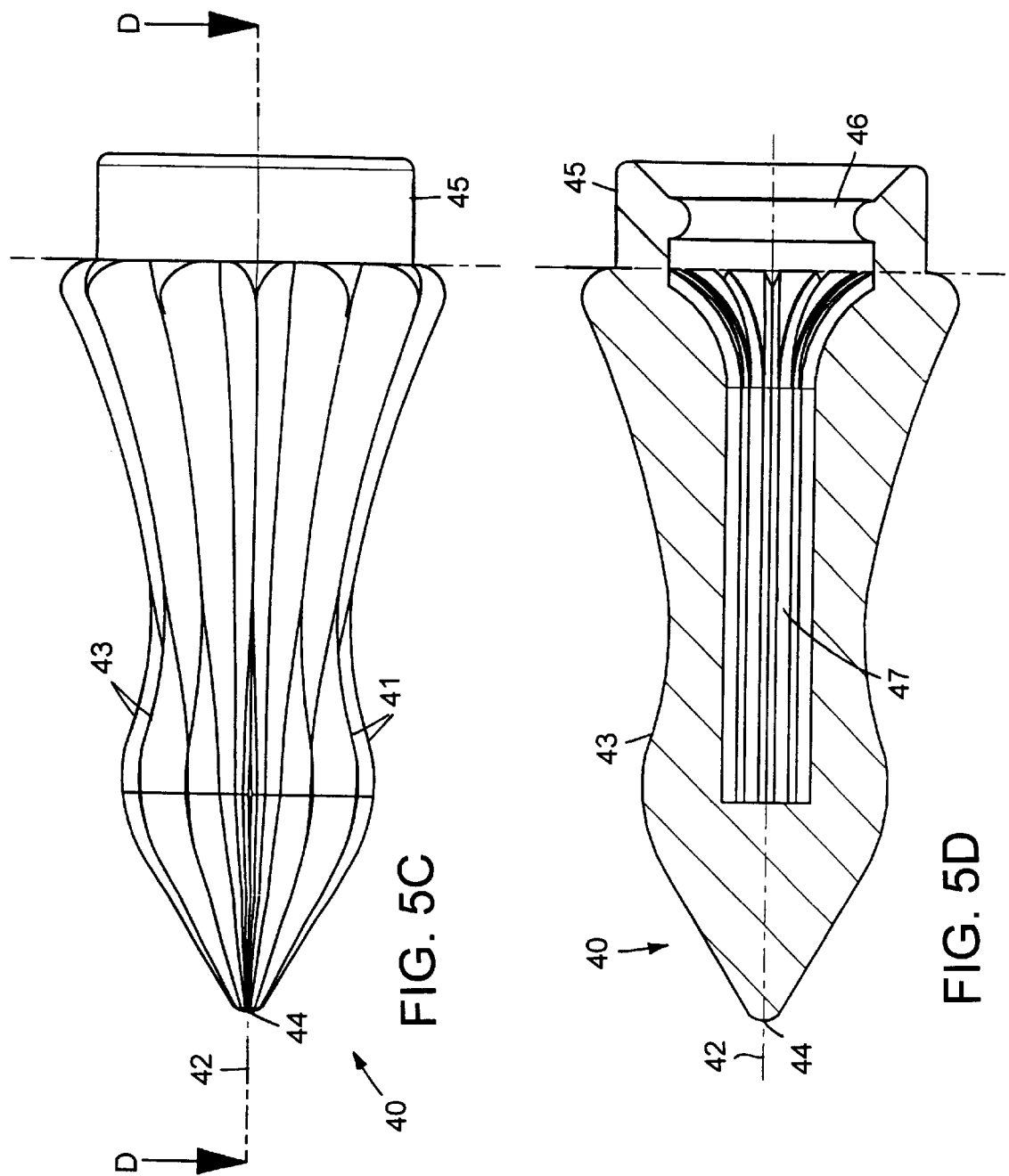

ELECTRICALLY OPERATED TOOTH-CLEANING DEVICE

CROSS REFERENCE TO RELATED APPLICATIONS

This application claims the benefit of U.S. Provisional patent application Ser. No. 60/044,148, filed Apr. 22, 1997.

BACKGROUND OF THE INVENTION

The invention relates to a tooth-cleaning device with a handle part provided with drive means, said handle part being connectable with an attachment provided with a cleaning tool, with the cleaning tool being capable of being given a rotary motion by the drive means. In addition, the invention relates to an attachment for a tooth-cleaning device, said tooth-cleaning device having a handle part provided with drive means, said handle being connectable with an attachment provided with a cleaning tool, with the cleaning tool being given a rotary motion by the drive means.

A tooth-cleaning device of this kind and an attachment of this kind for a tooth-cleaning device are known from international patent application WO 96/32903, which is incorporated into the content of the disclosure of the present patent application by express reference.

In that application, a tooth-cleaning device is described in which an attachment can be mounted on a handle part. An elongate, thin, and flexible cleaning tool is displaceably mounted in the attachment, said tool being suitable for cleaning the teeth, especially for cleaning the spaces between the teeth. A switch is provided on the handle part for switching the tooth-cleaning device on and off. When a user moves the switch in the direction of the attachment, the cleaning tool is caused to rotate or oscillate alternately around a lengthwise axis. In addition, the displacement of the switch causes the cleaning tool to be pushed out of the attachment. In this way, the user can clean in particular the spaces between the teeth with the aid of the driven cleaning tool. When the switch is returned to the initial position, the cleaning tool is pushed back into the attachment and the drive of the cleaning tool is switched off.

With the aid of the elongate, thin, and flexible cleaning tool it is possible to clean smaller spaces between the teeth. However, if the space between two teeth is larger, the abovementioned elongate, thin, and flexible cleaning tool is no longer suited for effective and proper interdental cleaning.

SUMMARY OF THE INVENTION

The goal of the invention is to provide an electrically driven tooth-cleaning device by which larger spaces between the teeth can also be cleaned in an optimum fashion.

This goal is achieved in a tooth-cleaning device of the species recited at the outset according to the invention by virtue of the fact that a first cleaning tool of a first attachment can be coupled directly to the drive means and that a second cleaning tool of a second attachment can be coupled by a transmission with the drive means. In an attachment for a tooth-cleaning device of the species recited at the outset, the goal is achieved according to the invention by virtue of the fact that the attachment has in particular a transmission with a pinion and a crown gear.

Therefore, according to the invention, two separate attachments with corresponding cleaning tools are provided, one for cleaning small spaces between the teeth and the other for cleaning larger spaces between the teeth. This makes it possible to adapt the individual cleaning tools optimally to the size of the space between the teeth. For smaller spaces between the teeth, an elongate, thin, and flexible cleaning tool is provided in particular. For larger spaces between the teeth, a cleaning tool resembling a brush in particular may be provided. In this manner it is possible to clean the larger spaces between the teeth in a correct and problem-free manner with the cleaning tool that resembles a brush. The smaller spaces between the teeth, for whose cleaning the cleaning tool resembling a brush is not suitable, can be cleaned effectively and properly with the thin, elongate, and flexible cleaning tool. By switching between the attachments with the respective cleaning tools, therefore, a user can optimally clean large and small spaces between the teeth without considerable effort.

In the case of the elongate, thin, and flexible cleaning tool for the smaller spaces between the teeth, it is advantageous for this cleaning tool to be driven at a high rotational speed. This rotational speed however is too high for the cleaning tool that resembles a brush. If the brush-like cleaning tool were driven at a high rotational speed, it could cause injury especially to the user's gums. The transmission according to the invention is provided for this purpose. With the aid of the transmission, it is possible for the two cleaning tools to be driven at different rotational speeds. Thus it is possible for the drive means to produce a low rotational speed and for the transmission to change this low rotational speed to a high rotational speed for the elongate, thin, and flexible cleaning tool. It is also possible for the drive means to produce a high rotational speed that is changed by the transmission to a lower rotational speed for the brush-like cleaning tool.

The user of the tooth-cleaning device according to the invention therefore can adapt the cleaning tools optimally to the existing spaces between the teeth. With the aid of the transmission, the individual cleaning tools can be driven at the optimum rotational speeds.

In a first advantageous embodiment of the invention the transmission is associated with the second attachment. Thus, the transmission is a part of the second attachment and is mounted therewith on the handle part. In this way it is possible for each cleaning tool to be driven at the optimum rotational speed by the transmission contained directly in the respective attachment. It is not necessary to change the handle part of the tooth-cleaning device. The rotational speed can be adapted especially simply and flexibly in this manner to whichever cleaning tool is being used.

In an improvement on the invention, a pinion that can be coupled with the derive means is provided in the second attachment, said pinion meshing with a crown gear connected with the second cleaning tool. This constitutes an especially simple and economically manufactured design for the transmission contained in the second attachment. With the aid of the transmission, the rotational speed is adapted to whichever cleaning tool is in use. Moreover, the abovementioned transmission can also be used to deflect the drive direction of the cleaning tool by approximately 90°. Another advantage of the transmission described consists in the fact that the axes do not have to be adjusted or fixed. The required axial retention of the crown gear can be achieved in a simple fashion with the aid of a lid or the like on the attachment.

It is especially advantageous for the second attachment to be made of plastic. In particular, manufacture of the transmission from plastic results in a considerable cost reduction.

In a second advantageous embodiment of the invention, the transmission is associated with the handle part. As a result of this design, it is no longer necessary for the transmission to be accommodated in the attachment. Improvements that also have a positive effect on function and manufacturing cost are also obtained as far as the design of the transmission is concerned.

In an advantageous improvement on the invention, a clutch is provided in the handle part, said clutch being connected nonrotatably with the drive means by gears, said clutch also being operable by the second attachment. In this way it is particularly advantageous for the actuated clutch to be connected nonrotatably with the second cleaning tool. It is possible to change the rotational speed of the cleaning tool with the aid of the clutch. In a non-actuated state of the clutch, the transmission that consists of the abovementioned gears does not operate, so that the rotational speed of the drive means is transmitted directly to the cleaning tool. On the other hand, if the clutch is in an actuated state, the rotational speed of the drive means is stepped up or down with the aid of the above gears. This means that the rotational speed of the cleaning tool will be higher or lower. In this way, the change in rotational speed for different cleaning tools can be accomplished with a single transmission.

It is especially advantageous for the transmission to be designed as a step-down transmission. In this way it is possible to operate even those tooth-cleaning devices that are already available and which are provided for the operation of elongate, thin, and flexible cleaning tools at a high rotational speed, with brush-like cleaning tools with a low rotational speed (rpm). It is especially advantageous in this regard for the transmissions according to the first embodiment described to be contained in the attachment. The attachment with the step-down transmission is mounted on the existing tooth-cleaning device. The high rpm of the drive means of the tooth-cleaning device is reduced by the transmission to an rpm that is suitable for driving the brush-like cleaning tool.

In a first advantageous embodiment, the second cleaning tool has bristles arranged at least in one or more planes at an angle to one another and projecting laterally from a shaft. In particular, the bristles can be arranged in two rows along the shaft and can be mounted essentially diametrically opposite one another on the shaft. Moreover, the bristles can also be provided in several planes at angles to one another, for example four rows of bristles can lie in two planes aligned approximately at right angles. The shaft is made long, thin, and flexile. The bristles project from the shaft at approximately right angles. With the bristles in a common plane, the cleaning tool can simply be inserted into an interdental space while it is shut off. When the user switches on the tooth-cleaning device, the interdental space will be impacted by the rotating bristles. The adjacent tooth surfaces will thus be scraped by the bristles and cleaned, especially of plaque, as a result.

In one advantageous improvement on the invention, the free ends of the bristles form a line that is curved toward the shaft. When the cleaning tool is introduced into an interdental space, this arrangement of the bristles means that not only the surfaces of the adjacent teeth that are directly opposite one another will be cleaned when the device is switched on, but also, as a result of the longer bristles, the adjoining proximal areas will be cleaned as well, both lingually and buccally.

It is especially advantageous for the second cleaning tool to be made of plastic. In this case, the cleaning tool can be manufactured in simple fashion by using a plastic injection molding method. In particular, arranging the bristles in a common plane facilities such manufacture. The cleaning tool advantageously constitutes a separate part that can be mounted in particular on the crown gear of the transmission contained in the attachment. Consequently, it is possible to remove the cleaning tool from the attachment, for example after use, and to clean it. A new cleaning tool can then be mounted on the attachment for the next interdental cleaning.

In a second embodiment, the second cleaning tool can have strips arranged approximately in the shape of a star around an axis, with the edges of said strips being are aligned approximately parallel to one another. This cleaning tool is provided in particular for larger interdental spaces. With the aid of the strips it is possible to free the surfaces of the adjoining teeth of plaque in particular.

It is especially advantageous for the edges of the strips to have a shape that is curved toward the axis. This ensures that not only the surfaces of the adjacent teeth that are directly opposite one another will be impacted by the cleaning tool, but also that the lingual and buccal tooth surfaces will be cleaned at the same time.

Additional features, possible applications, and advantages of the invention follow from the description below of embodiments of the invention shown in the figures of the drawing. All of the features described or shown, either individually or in any combination, constitute the subject of the invention, regardless of their combination in the claims or their back references and independently of their wording or representation in the specification or the drawing.

Other advantages and features will become apparent from the following description of the preferred embodiment and from the claims.

BRIEF DESCRIPTION OF THE DRAWINGS

FIG. 4a shows a schematic section through the attachment in FIGS. 1 and 3 along plane A—A in FIG. 4b;

FIG. 4b shows a schematic section through the attachment in FIGS. 1 to 3 along plane B—B in FIG. 4a;

FIG. 4c shows a schematic section through the attachment in FIGS. 1 to 3 along plane C—C in FIG. 4a;

FIGS. 5a to 5c show a schematic perspective view, a top view, and a side view of a second embodiment of a cleaning tool according to the invention;

FIG. 5d shows a schematic section of the cleaning tool in FIGS. 5a to 5c along a plane D—D in FIG. 5c;

DESCRIPTION OF THE PREFERRED EMBODIMENTS

Figure 1A:
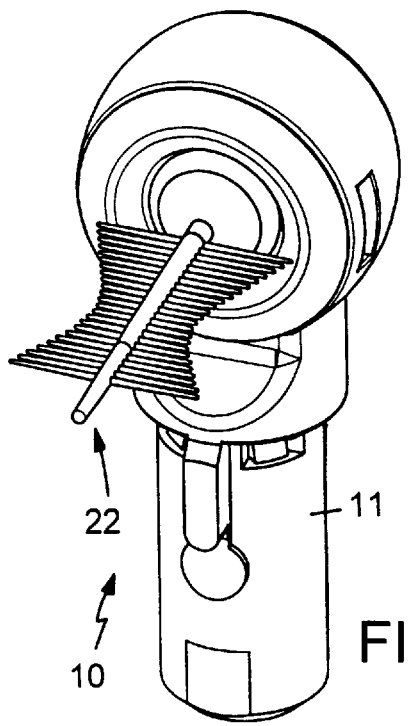
FIGS. 1a and 1b show schematic perspective views of a first embodiment of an attachment according to the invention with a first embodiment of a mounted cleaning tool according to the invention for an electrically operated tooth-cleaning device.
Figure 2:
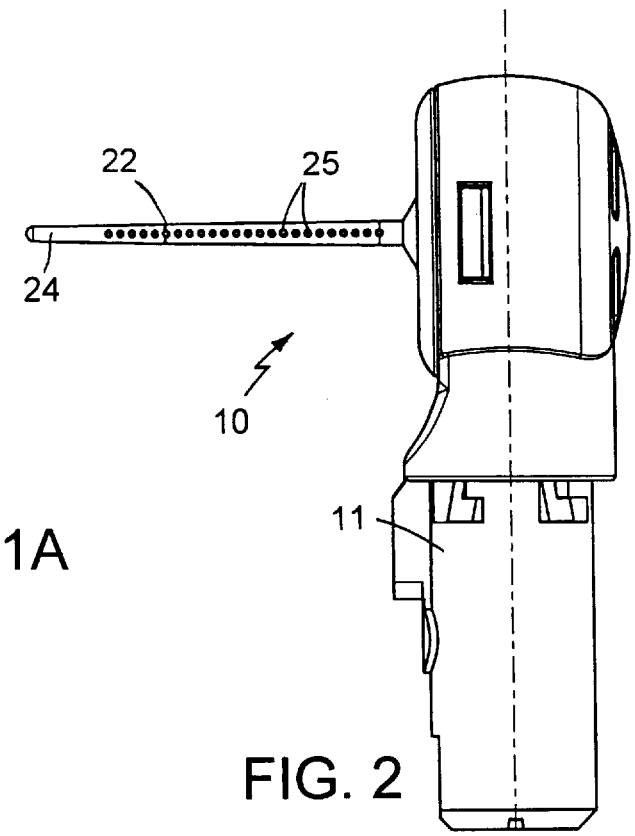
FIG. 2 shows a schematic side view of the attachment of FIGS. 1a and 1b.
Figure 1B:
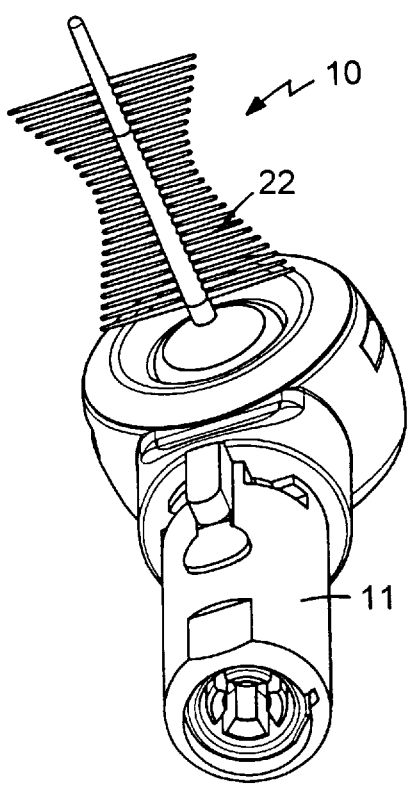
Figure 3:
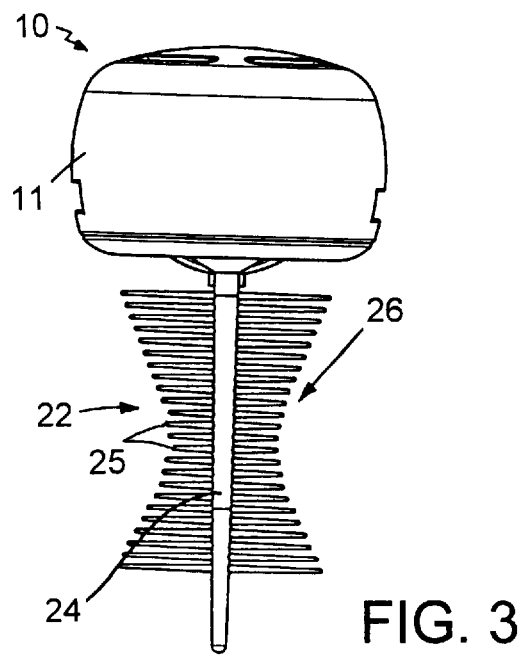
FIG. 3 shows a schematic view of the attachment of FIGS. 1a, 1b, and 2.

In international patent application WO 96/32903, to which express reference is hereby made and whose disclosure contents are hereby incorporated into the present patent application, an electrically operated tooth-cleaning device is described in which an attachment can be mounted on a handle part. An electric motor is accommodated in the handle part as a drive means, said motor driving a drive shaft at a predetermined high rotational speed. The rotational speed is approximately 3500 rpm for example. An attachment can be mounted on the tubular free end of the handle part. An elongate, thin, and flexible cleaning tool is displaceably accommodated in the attachment. With the attachment mounted and with the unit switched off, the cleaning tool remains inside the attachment. When the tooth-cleaning device is switched on by moving a switch, the cleaning tool is pushed out of the attachment. At the same time, the electric motor is switched on so that the cleaning tool, coupled to the drive shaft, is set rotating. The user can now clean especially narrow interdental spaces with the aid of the rotating cleaning tool. When the switch is moved back into its initial position, the electric motor is switched off and the cleaning tool is pushed back into the attachment at the same time.

An attachment 10 is shown in FIGS. 1 to 4 which, in place of the attachment described in international patent application WO 96/32903, can be mounted on the handle part of the electrically operated tooth-cleaning device.

Attachment 10 has a housing 11 whose dimensions are adapted to the tubular free end of the handle part. Attachment 10 can thus be connected shapewise with the handle part.

A shaft 12 is accommodated inside attachment 10, said shaft being designed at its end 13 facing the tubular free end of the handle part such that it can be coupled nonrotatably, possibly by additional shafts, with the drive shaft of the electric motor. For this purpose, shaft 12 is provided with slots 14 or the like for example. Pinion 15 is provided at the opposite end of shaft 12. Shaft 12 has two annular projections 16 with whose aid shaft 12 can be secured and mounted inside housing 11 of attachment 10.

In addition, a crown gear 17 is accommodated in attachment 10, said gear meshing with pinion 15. The axis of crown gear 17 is aligned at approximately 90° to the axis of pinion 15 and thus to the axis of shaft 12. Crown gear 17 has a larger number of teeth than pinion 15. Crown gear 17 is mounted on a pin 18 or the like inside attachment 10. In addition, attachment 10 has a lid 19 that holds crown gear 17 inside attachment 10.

Lid 19 has an approximately circular opening 20 through which a cylindrical part 21 of crown gear 17 extends. A cleaning tool 22 is mounted on this cylindrical part 21. For this purpose, the cleaning tool has an approximately pot-shaped recess 23 by which it can be mounted on cylindrical part 21 of crown gear 17.

Attachment 10, especially pinion 15 and crown gear 17, is and/or are made of plastic.

The cleaning tool 22 described below is a first embodiment of a cleaning tool which can be used together with attachment 10 described above. Of course the cleaning tool can also be used in conjunction with a separate handle with a rotating or oscillating drive, without attachment 10.

Cleaning tool 22 has a shaft 24 connected with pot-shaped recess 23. The axis of shaft 24, the axis of recess 23, cylindrical part 21 of crown gear 17, and crown gear 17 itself are arranged approximately coaxially with respect to one another.

A plurality of bristles 25 extends approximately at right angles from shaft 24. All bristles 25 are arranged essentially in a common plane. Bristles 25 are arranged in two rows on opposite sides of shaft 24. The individual bristles 25 are spaced approximately equally apart from one another. The lengths of bristles 25 in a row are selected so that tips 26 of bristles 25 form a curved line. The bottom of this curved line is directed toward shaft 24. Thus, bristles 25 at the two ends of the bristles forming a row are the longest while bristles 25 in the middle of the row are the shortest.

The diameter of shaft 24 is approximately 1 mm. Bristles 25 are mounted over a length of about 1 cm on shaft 24. Shaft 24 thus projects beyond bristles 25. The individual bristles 25 have a diameter of approximately 1/10 mm and are rounded at the tips. The longest bristles 25 are about 4 mm long while the shortest bristles are about 2 mm long.

Numerous modifications of cleaning tool 22 are possible and may be advantageous as well. Bristles 25 can be arranged in one row, especially two rows, or even more, for example four rows, on shaft 24. The last embodiment is the subject of the diagram in FIG. 9. The rows can also be mounted pairwise, essentially diametrically opposite one another, on shaft 24 of cleaning tool 22. Shaft 24, like bristles 25, consists of a flexible, especially a highly flexible, material, with shaft 24 and bristles 25 being connected integrally with one another. Flexible bristles 25, in a resting position, in other words when cleaning tool 22 is not in use, are located essentially parallel to one another within a row and are preferably aligned at right angles to shaft 24. Bristles 25 can be deflected from the resting position by the application of an external force, and when the action of the force is eliminated, bristles 25 return in a spring-elastic manner to the resting position. Shaft 24 is also designed to be rotationally symmetrical. Recess 23 at the foot of shaft 24 serves for mounting on a rotating or alternately oscillating drive. The free end of the shaft has a tip without bristles to facilitate insertion of cleaning tool 22 into interdental spaces. Cleaning tool 22 is designed essentially rotationally symmetrically especially with an angle of symmetry angle of 60°, 90°, 120° or 180°. In the vicinity of recess 23, shaft 24 has a shaped outer surface that facilitates mounting cleaning tool 22 on the rotary drive. The outer surface can have a groove-shaped recess or the like. Preferably at least a portion of the adjacent bristles 25 in a row have a different length. In this way, the length of bristles 25 in a row decreases from a first maximum value at the free end of cleaning tool 22, especially continuously, to a minimum value and increases from the minimum value, continuously once again, to a second maximum value. In particular, the first and second maximum values are essentially the same. Moreover, the free ends of bristles 25 are rounded. The diameter of bristles 25 also decreases from the shaft toward the free end. Of course, the data on the positioning of bristles 25 on shaft 24 relate to a period of time when cleaning tool 22 is not in use. Flexible shaft 24, during the use of cleaning tool 22, may undergo at least partially nonreversible twisting, with the result that the bristles are no longer arranged in at least one or more common planes, but may be in the form of a spiral.

Figure 9:
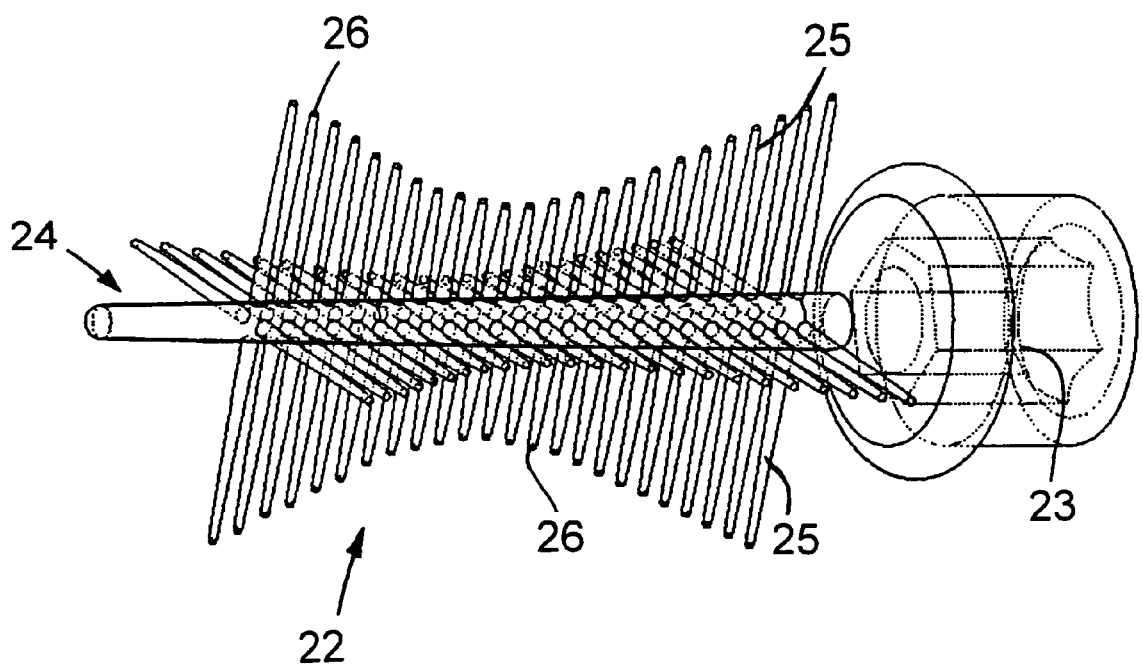
FIG. 9 is another embodiment of a cleaning tool in a perspective view.

While cleaning tool 22 in FIGS. 1, 2, 3, and 4 has bristles 25 arranged essentially diametrically opposite one another in two rows on shaft 24, FIG. 9 shows a cleaning tool 22 that has four rows of bristles 25, with the adjacent rows of bristles 25 forming an essentially right angle between them. In this case, the bristles are arranged essentially in two planes that form an angle of 90° between them. Of course, other positions are possible for bristles 25 arranged in rows on shaft 24. The type of mounting and positioning of bristles 25 on shaft 24 is determined essentially by the limitations imposed by injection molding technology, particularly the ease with which the injection-molded part can be removed from the injection mold and the complexity of the injection mold itself.

Cleaning tool 22 is made of a plastic, especially a thermoplastic elastomer. The surface of cleaning tool 22, especially the surface of bristles 25, is smooth and can be coated. Cleaning tool 22 is made by a plastic injection molding process.

For interdental cleaning, the user can locate the interdental space to be cleaned with the aid of projecting shaft 24. Then the user introduces cleaning tool 22 into the interdental space, especially in such fashion that the plane formed by bristles 25 is aligned approximately parallel to the interdental space formed by the two teeth that are opposite one another. Then the user switches on the tooth-cleaning device by means of the switch. As a result, cleaning tool 22 is coupled nonrotatably with the electric motor. Cleaning tool 22 is thereby set rotating around the axis formed by shaft 24.

With rotating cleaning tool 22, bristles 25 pass over the tooth surfaces in the interdental space that are opposite one another. The shorter bristles impact the approximately ventral tooth surfaces of the interdental space, while the longer bristles 25 reach the adjoining tooth surfaces both lingually and buccally.

Figure 5B:
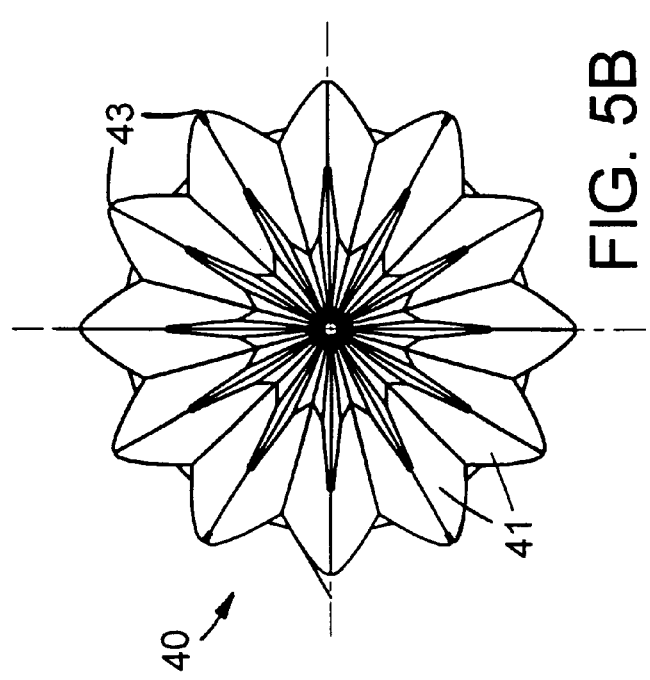
Figure 5A:
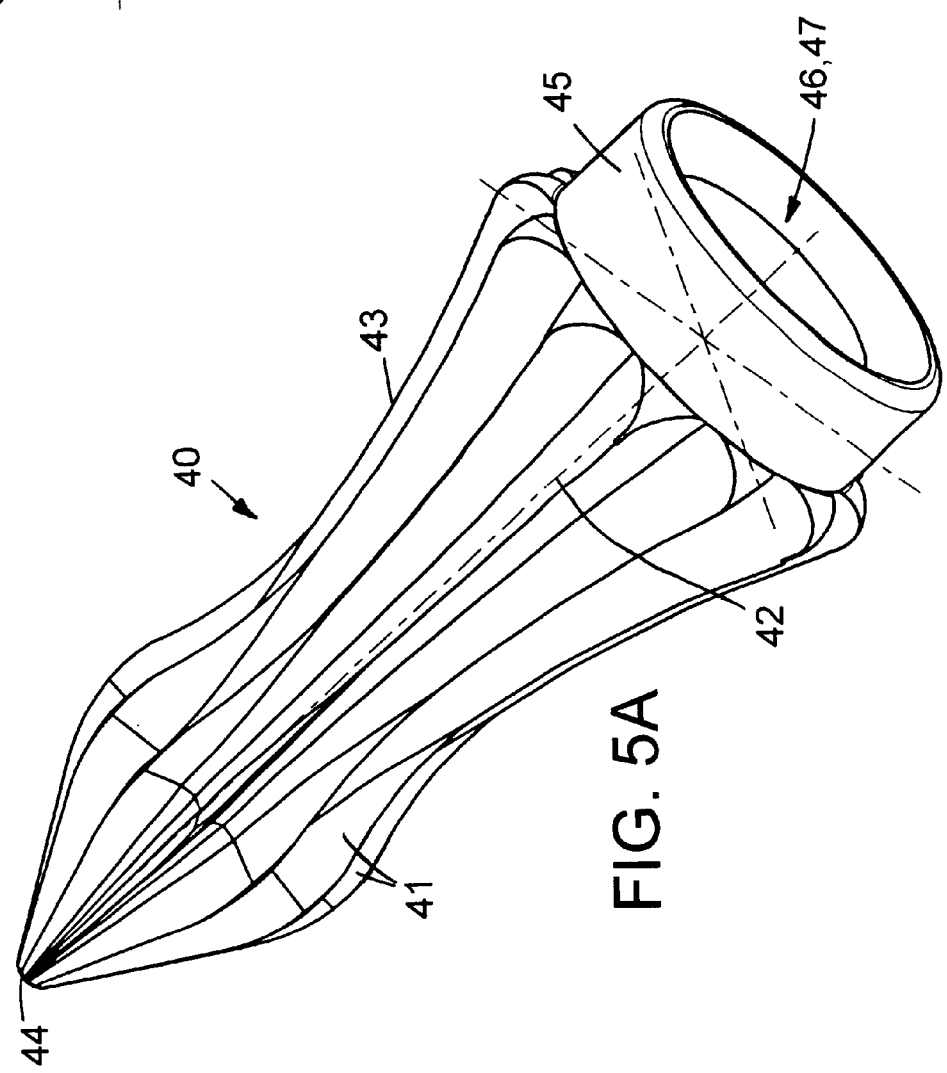

FIGS. 5 and 6 show two additional embodiments of cleaning tools which can be mounted on attachment 10 instead of the cleaning tool 22 shown in FIGS. 1 to 4.

FIGS. 5a to 5d show a cleaning tool 40 made approximately conical. A plurality of strips 41 projects from the jacket surface of cleaning tool 40, said strips, as is especially clear from FIG. 5b, being arranged in the shape of a star with respect to an axis 42. The individual strips 41 each have an edge 43, all of said edges being aligned toward cone tip 44. Otherwise, the edges run approximately parallel to one another and are arranged approximately parallel to axis 42.

As is particularly evident from FIG. 5d, the approximately conical cleaning tool 40 deviates from the conical shape in an area adjacent to cone tip 44. At this point, cleaning tool 40 is provided with a thickening such that edges 43 of strips 41 have a pattern that is curved in the direction of axis 42. The diameter of cleaning tool 42 is thus at its largest in the vicinity of its foot 45. Then the diameter decreases until it reaches a local minimum approximately at the center. Then the diameter of cleaning tool 40 increases again until it reaches a local maximum in the vicinity of the thickening. Then the diameter of cleaning tool 40 decreases approximately uniformly toward cone tip 44.

In the vicinity of foot 45, cleaning tool 40 is provided with a recess 46 such that it can be mounted on cylindrical part 21 of crown gear 17 of the attachment 10 shown in FIGS. 1 to 4.

Additionally or alternatively thereto, the interior of cleaning tool 40 is provided with a recess 47 that has a plurality of lengthwise grooves. By means of this recess 47, cleaning tool 40 can be mounted on a suitably shaped pin. This pin can be provided for example instead of a brush head on an electric toothbrush, like that described for example in international patent application WO 94/12121. In this way it is possible for cleaning tool 40 to be mounted on an electric toothbrush. A user can then also clean spaces between the teeth with the electric toothbrush, with the aid of the electric toothbrush and cleaning tool 40 of the electric toothbrush mounted thereon. In this case, the pin and hence cleaning tool 40 can be driven to rotate or oscillate alternately. The transmission contained in attachment 10 is not provided in this case and also is not required since the rotational speed of electric toothbrushes is smaller than the rotational speed of the electrically driven tooth-cleaning device according to international patent application WO 96/32903.

Figure 6A:
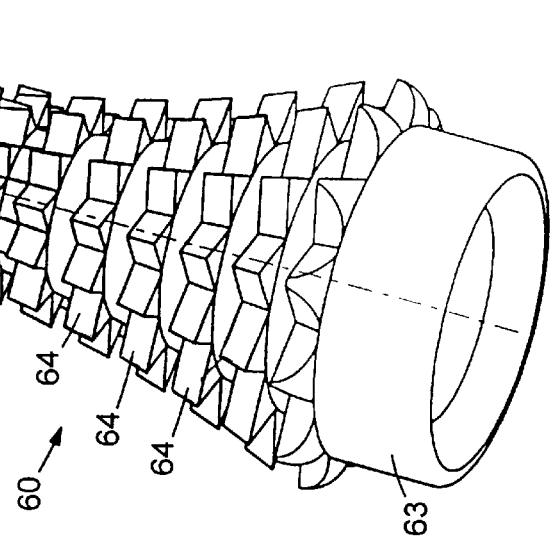
FIGS. 6a to 6c show a schematic perspective view, top view, and rear view of a third embodiment of a cleaning tool according to the invention.
Figure 6D:
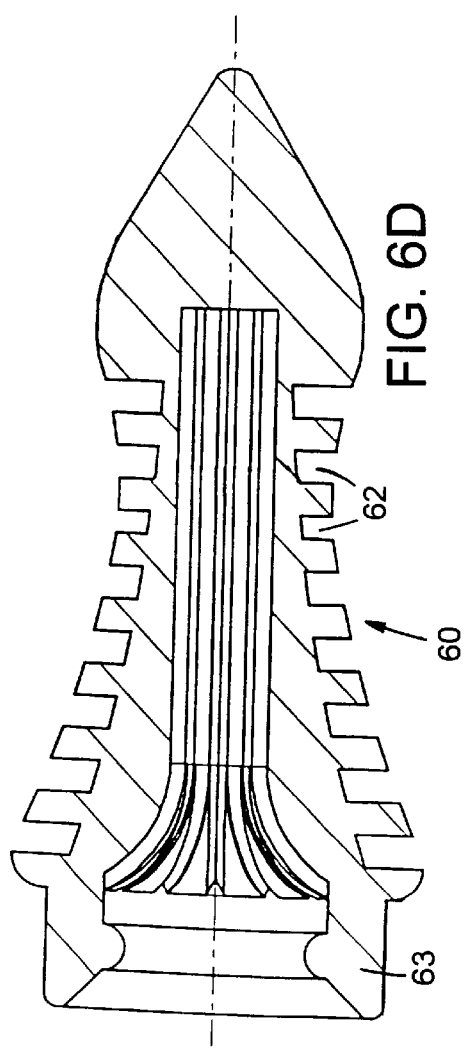
FIG. 6d shows a schematic lengthwise section through the cleaning tool in FIGS. 6a to 6c.
Figure 6B:
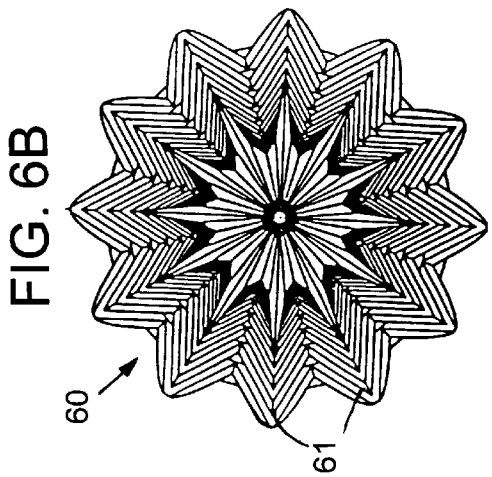
Figure 6C:
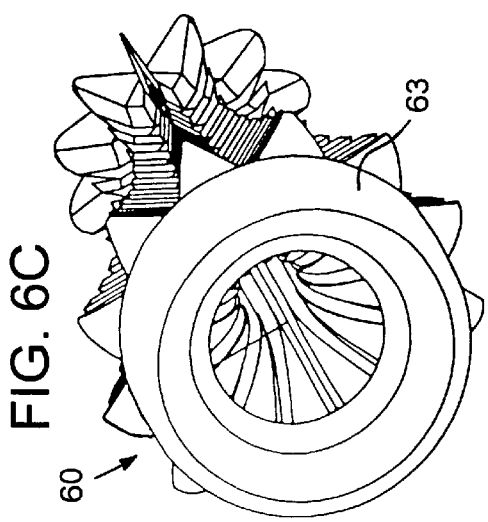

FIGS. 6a to 6d show a cleaning tool 60 that essentially corresponds to cleaning tool 40 in FIGS. 5a to 5d. Cleaning tool 60 differs from cleaning tool 40 in that not only are strips 61 provided on the jacket of approximately conical cleaning tool 60 but a plurality of depressions 62 in the shape of a circle is provided as well. These depressions 62, as can be seen in particular from FIG. 6d, are provided only in the area of foot 63, up to a point shortly before the area of local maximum diameter of cleaning tool 60. In this area, a plurality of teeth 64 is formed because of depressions 62 in strips 61.

Like cleaning tool 40, cleaning tool 60 can also be mounted on attachment 10 shown in FIGS. 1 to 4. It is also possible to mount cleaning tool 60 on a corresponding pin of an electric toothbrush. Cleaning tools 40, 60 are made of a plastic, especially a thermoplastic elastomer.

Regardless of the cleaning tool used, in attachment 10 the high rotational speed of the tooth-cleaning device is stepped down with the aid of the transmission composed of pinion 15 and crown gear 17 to a lower rotational speed. The drive can be one that rotates or one that can also oscillate alternately. If cleaning tool 22 is used, it is suitable for spaces between the teeth that are larger than 1.5 mm in particular. Cleaning tools 40 and 60 are provided for spaces between the teeth that are much larger than 1.5 mm. The design of cleaning tools 22, 40, 60 especially because of the curved pattern of tips 26 and/or strips 41, 61, means that not only can the tooth surfaces opposite one another in the interdental space be cleaned, but that bristles 25 and/or strips 41, 61 can also reach the proximal areas of the teeth both lingually and buccally.

Figure 7A:
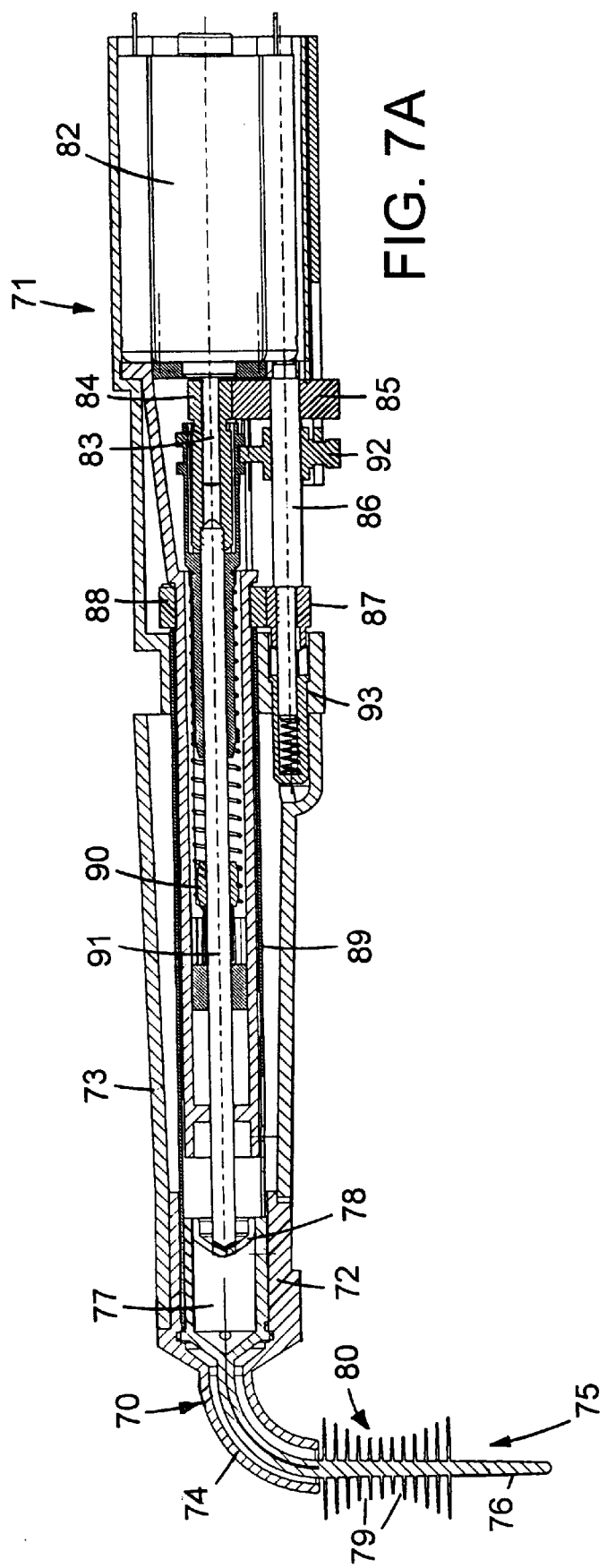
FIGS. 7a and 7b show schematic lengthwise sections through a second embodiment of an attachment according to the invention for an electrically operated tooth-cleaning device.
Figure 7B:
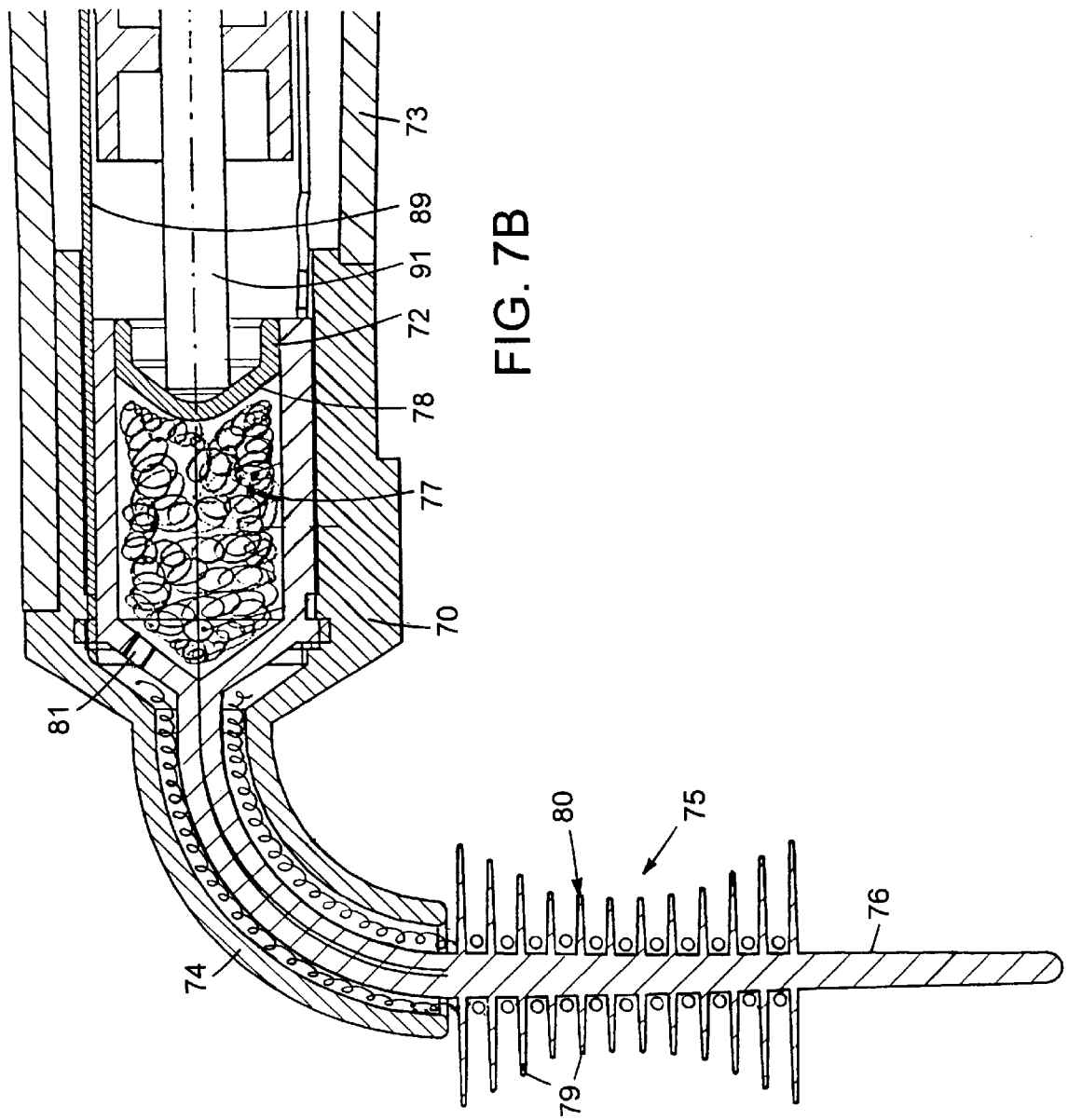

FIGS. 7a and 7b show an attachment 70 that can be mounted on an electrically operated tooth cleaning device 71. For this purpose, attachment 70 is designed at its end 72 facing tooth-cleaning device 71 such that it can be inserted shapewise into a tubular housing part 73. Housing part 73 in turn can be mounted on the tubular free end of the handle part of tooth-cleaning device 71.

Attachment 70 has a tube 74 curved in the shape of an arc of approximately 90°, through which tube a cleaning tool 75 is passed. Cleaning tool 75 has an elongate, thin, and flexible shaft 76 that follows the curvature of tube 74. Inside attachment 70, and shaft 76 is connected with a storage compartment 77. Storage compartment 77 is made cylindrical and designed to hold toothpaste or the like. Storage compartment 77 is closed by a lid 78.

In its area that projects from tube 74, shaft 76 is provided with a plurality of bristles 79. Bristles 79 project approximately at right angles from shaft 76. Bristles 79 are arranged on both sides of shaft 76 and form a common plane. The number of bristles 79 is the same on both sides of shaft 76.

The length of bristles 79 is such that tips 80 of bristles 79 form a curved line on each of the two sides of shaft 76, said line curving toward shaft 76. In this way, the first and last bristles 79 on each of the two sides of shaft 76 are the longest while the shortest bristles are located at the middles of the respective rows of bristles 79.

Shaft 76 projects beyond the area in which bristles 79 are located.

Figure 8A:
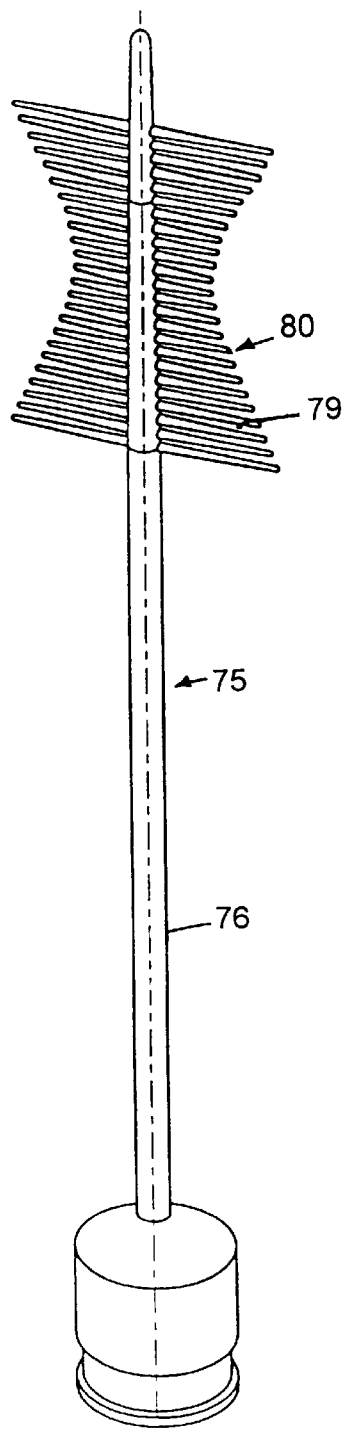
FIGS. 8a and 8b show a schematic perspective view and side view of a cleaning tool according to the invention, for example for the attachment in FIGS. 1 to 4 or 7a and 7b.
Figure 8B:
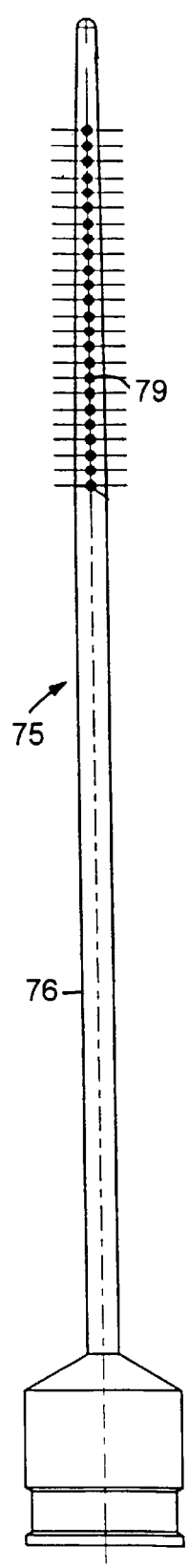
Figure 8C:
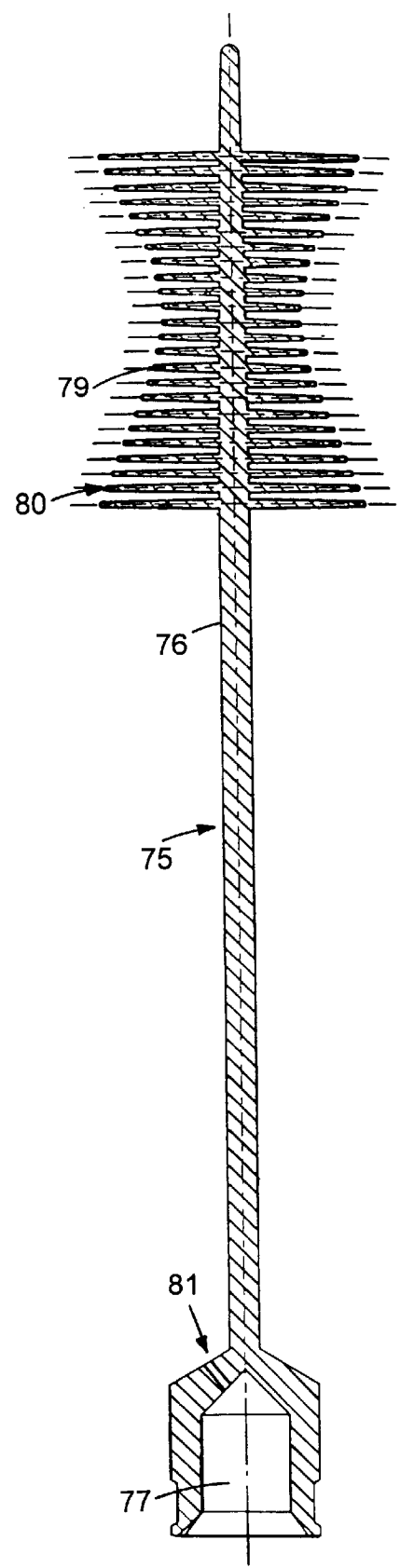
FIG. 8c shows a schematic lengthwise section through the cleaning tool in FIGS. 8a and 8b.

Cleaning tool 75 is shown as a separate part in FIG. 8a to 8c. In those figures, it is possible to see the path of tips 80 of bristles 79, curved toward shaft 76, as well as the arrangement of all the bristles 79 in a common plane. In addition it is evident from FIG. 8c that an opening 81 is provided in the vicinity of storage compartment 77 that connects storage compartment 77 with the exterior. Of course cleaning tool 75 can also be used in conjunction with attachment 10 or another rotary drive, with storage compartment 77 then serving as a recess 23 for coupling cleaning tool 75 to the rotary drive.

It is evident from FIG. 7b that toothpaste for example can escape from storage compartment 77 through opening 81 and can then pass through tube 74 to bristles 79. For this purpose, it is necessary for the material contained in storage compartment 77 to have a pasty or even liquid state, so that it can be forced through opening 81 from storage compartment 77 by the aid of a forward motion of lid 78 for example.

According to FIG. 7a, tooth-cleaning device 71 is provided with an electric motor 82 that drives a drive shaft 83. Drive shaft 83 is connected nonrotatably with a gear 84 meshing with a gear 85. Gear 85 drives a shaft 86 on which a gear 87 is rotatably mounted. Gear 87 meshes with a gear 88, connected nonrotatably with a tube 89. Gear 88 and tube 89 are mounted coaxially with respect to drive shaft 83 and are rotatably mounted inside tooth-cleaning device 71.

Drive shaft 83 is also coupled by a slip clutch 90 with a shaft 91 located inside tube 89, said shaft being capable of being pushed back and forth in the lengthwise direction with the aid of a switch 92.

A clutch 93 is provided in the vicinity of the free end of shaft 86 that projects beyond gear 87. Clutch 93 is nonrotatably connected with shaft 86. In addition, clutch 93 can be displaced lengthwise on shaft 86. With the aid of a spring 94, clutch 93 is pushed away from gear 87 when it is in its non-operating state. In this non-operating state of clutch 93, there is no connection between shaft 86 and gear 87. As a result, with tooth-cleaning device 71 in the switched-on state, and with clutch 93 not operating, tube 89 does not perform any rotary motion. only shaft 91 is rotated by slip clutch 90.

However, if housing part 73, as shown in FIG. 7a, is mounted on the housing, especially on tube 89 of tooth-cleaning device 71, clutch 93 is displaced and is then in its operating state. In this case, there is a non-rotating connection between clutch 93 and gear 87. This means that gear 87 is nonrotatably coupled with shaft 86 through clutch 93. With tooth-cleaning device 71 switched on, tube 89 is caused to rotate by clutch 93 and shaft 86. At the same time, shaft 91 is also caused to rotate by slip clutch 90.

If housing part 73 is not mounted on tooth-cleaning device 71, an attachment can be mounted on the tubular end of tooth-cleaning device 71, as is known from international patent application WO 96/32903. In this case, the cleaning tool of the mounted attachment is caused to rotate through slip clutch 90 by shaft 91 when tooth-cleaning device 71 is in the switched-on operating state. Clutch 93 is in its non-actuated state. Tube 89 does not perform any rotary motion.

The abovementioned known attachment can be used to replace attachment 70 with corresponding housing part 73. In this case, housing part 73 is mounted on the housing of tooth-cleaning device 71. As a result, the clutch is shifted into its actuated state. Attachment 70 with cleaning tool 75 is then mounted on housing part 73. This produces a non-rotatable connection between cleaning tool 75 and tube 74, especially through storage compartment 77 of cleaning tool 75.

With tooth-cleaning device 71 in the switched-on operating state, tube 89 is caused to perform a rotary motion by clutch 93. As a result, cleaning tool 75 also rotates. Because of the flexibility of shaft 76 of cleaning tool 75, this rotation is conveyed to bristles 79.

In the switched-on operating state, shaft 91 also rotates. This rotation however is not transmitted any further. Instead, shaft 91 serves to move lid 78 of storage chamber 77 as a result of a displacement of switch 92. When a user operates switch 92, the toothpaste contained in storage compartment 77 is forced out through opening 81 as a result and then passes through tube 74 to bristles 79. This is especially clear from FIG. 7b.

In the tooth-cleaning devices described above, provision is made such that cleaning tools 22, 40, 60, and 75 are caused to rotate. However it is likewise possible for cleaning tools 22, 40, 60, and 75 to perform another rotary motion, especially an alternating oscillating rotary motion. As was mentioned above in connection with cleaning tools 40, 60, it is also possible for cleaning tools 22, 40, 60, and 75 described above to be used in conjunction with an electric toothbrush, which in particular performs an alternating, oscillating rotary motion.

The invention is meant to cover all of the abovementioned alternative approaches as well as others not specifically mentioned. The above-mentioned embodiments and others are within the following claims.

What is claimed is:

1. Tooth-cleaning device comprising:
   a handle part provided with drive motor;
   a first attachment including a first cleaning tool which connects directly to the handle part and is caused by the drive motor to perform rotary motion during use;
   a second attachment including a second cleaning tool; and
   a transmission associated with either the second attachment or the handle part and which serves to connect the second cleaning tool to the handle part and which is caused by the drive motor to perform rotary motion during use.

2. The tooth-cleaning device according to claim 1, wherein the transmission is associated with the second attachment.

3. The tooth-cleaning device according to claim 2, wherein the transmission comprises a pinion that is coupled with the drive motor during use, and a crown gear meshing with the pinion, said second cleaning tool coupling with said crown gear.

4. The tooth-cleaning device according to claim 2, wherein the second cleaning tool is made of plastic or metal.

5. The tooth-cleaning device according to claim 1 wherein the transmission is associated with the handle part.

6. The tooth-cleaning device according to claim 5, wherein the handle part comprises a clutch and gears nonrotatably connecting the clutch with the drive motor, said clutch operable by the second attachment.

7. The tooth-cleaning devices according to claim 6, wherein the clutch is connected nonrotatably with second cleaning tool when actuated.

8. The tooth-cleaning device according to claim 1, wherein the transmission is designed as a step-down transmission.

9. The tooth-cleaning device according to claim 1, wherein the first cleaning tool is capable of cleaning spaces between the teeth that are smaller than approximately 1.5 mm.

10. The tooth-cleaning device according to claim 1, wherein the second cleaning tool is provided for cleaning spaces between the teeth that are larger than approximately 1.5 mm.

11. The tooth-cleaning device according to claim 10, wherein the second cleaning tool comprises a shaft and bristles arranged in a common plane and projecting from said shaft.

12. The tooth-cleaning device according to claim 11, wherein the free ends of the bristles lie along a curve that is convex relative to said shaft.

13. The tooth-cleaning device according to claim 10, wherein the second cleaning tool has strips that are arranged approximately in the shape of a star around an axis, and whose edges are aligned approximately parallel to one another.

14. The tooth-cleaning device according to claim 13, wherein the edges of strips have a pattern that curves toward the axis.

15. The tooth-cleaning device according to claim 10, wherein the second cleaning tool is made of plastic.

16. A tooth-cleaning attachment for coupling to a handdle part provided with drive motor, said attachment comprising:
    a tooth-cleaning tool which during operation is caused to rotate by said drive motor; and
    a transmission for coupling rotation generated by said drive motor to said cleaning tool, said transmission including a crown gear and a pinion that meshes with said crown gear, wherein the tooth-cleaning tool includes a shaft having a longitudinal axis and bristles projecting from said shaft, wherein said bristles are essentially arranged in at most two planes so that there are no bristles projecting from said shaft that are not arranged in any of the at most two planes and wherein the longitudinal axis of the shaft lies in each of the at most two planes.

17. The tooth-cleaning attachment according to claim 16 wherein bristles arranged essentially in only one common plane.

18. The attachment according to claim 16, wherein the transmission and tooth-cleaning tool are made of a plastic.

19. A tooth-cleaning attachment for coupling to a handle part provided with a drive motor, said attachment comprising:
    a tooth-cleaning tool which during operation is caused to rotate by said drive motor;
    a storage compartment that has at least one opening to the outer surface of the tooth-cleaning tool; and
    a housing which holds the tooth-cleaning tool and the storage compartment and which has at one end a coupling portion for coupling the tooth-cleaning attachment to the handle part and enabling the drive motor to rotate the tooth-cleaning tool.

20. The attachment according to claim 19, wherein toothpaste or the like is contained in the storage compartment.

21. The attachment according to claim 19, further comprising a transmission.

22. The attachment according to claim 16, wherein the bristles are located essentially in two planes that enclose an angle between them that is greater than 0°.

23. The attachment according to claim 22, wherein the bristles are arranged in at least two rows along said shaft.

24. The attachment according to claim 23, wherein the bristles are fastened in rows pairwise, essentially diametrically opposite one another on said shaft.

25. The attachment according to claim 16, wherein the shaft and bristles are made of a flexible material.

26. The attachment according to claim 16, wherein the shaft and bristles are connected integrally with one another.

27. The attachment according to claim 24, wherein the bristles in each row are aligned essentially parallel to one another in a resting position.

28. The attachment according to claim 16, wherein the bristles have a resting position in which the bristles are aligned essentially parallel to one another, and wherein the bristles can be deflected from the resting position under the influence of force, with the bristles returning in a spring-elastic manner to the resting position when not exposed to the action of force.

29. The attachment according to claim 16, wherein the shaft is made of a thermoplastic elastomer.

30. The attachment according to claim 16, wherein the shaft is designed to be rotationally symmetrical.

31. The attachment according to claim 17, wherein the shaft is uncoated.

32. The attachment according to claim 17, wherein the shaft is coated.

33. The attachment according to claim 16, wherein the shaft has a recess at one end for mounting on a rotating drive.

34. The attachment according to claim 17, wherein the shaft has a tip that is free of bristles.

35. The attachment according to claim 16, wherein the tooth cleaning tool is designed to be essentially rotationally symmetric with an angle of symmetry of 60°, 72°, 90°, 120°, or 180°.

36. The attachment according to claim 33, wherein the shaft has a shaped outer surface in the vicinity of the recess.

37. The attachment according to claim 36, wherein the outer surface has a groove-shaped recess.

38. The attachment according to claim 17, wherein adjacent bristles in the one common plane have different lengths.

39. The attachment according to claim 17, wherein the length of bristles in the one common plane decreases continuously from a first maximum value to a minimum value and rises again from the minimum value to a second maximum value.

40. The attachment according to claim 39, wherein the first and second maximum values are essentially the same.

41. The attachment according to claim 17, wherein the free ends of bristles are rounded.

42. The attachment according to claim 17, wherein the diameter of bristles decreases starting at shaft and extending toward the free end.

43. The attachment according to claim 16, wherein the shaft is flexible, and wherein the shaft undergoes torsion during the process of cleaning the interdental spaces.

44. The attachment according to claim 43, wherein the torsion on shaft is at least partially irreversible.

45. A tooth cleaning tool for attachment to a hand held unit including a motor driven output shaft, said tool comprising:
    an elongated shaft having an axis;
    a coupling member at one end of said elongated shaft which during use couples to the output shaft of the hand held unit; and
    a plurality of bristles attached to said elongated shaft, there being at least two intersecting imaginary planes whose intersection is substantially coincident with the axis of the elongated shaft and wherein said plurality of bristles lie substantially in at least one of said intersecting planes, wherein the end of said elongated shaft that is remote from the end having the coupling member is free of bristles over a substantial distance.

46. The tooth cleaning tool of claim 45 wherein all of said plurality of bristles lie substantially in one of said intersecting planes.

47. The tooth cleaning tool of claim 45 wherein said plurality of bristles constitutes all bristles attached to the elongated shaft.

48. The tooth cleaning tool of claim 46 wherein said plurality of bristles are distributed among two rows, a first row attached to a first side of said elongated shaft and a second row attached to a side of said elongated shaft that is opposite from the first side.

49. The tooth cleaning tool of claim 48 wherein the free ends of the bristles in each of the two rows lie along a corresponding smooth curve.

50. The tooth cleaning tool of claim 49 wherein said each of said corresponding smooth curves is convex relative to the elongated shaft.

51. The tooth cleaning tool of claim 45 wherein said plurality of bristles are distributed in both of said two planes.

52. The tooth cleaning tool of claim 51 wherein said plurality of bristles are distributed among four different rows of bristles.

53. The tooth cleaning tool of claim 52 wherein each of said four rows of bristles contains an equal number of bristles.

54. The tooth cleaning tool of claim 53 wherein said plurality of bristles constitutes all bristles attached to the elongated shaft.

55. The tooth cleaning tool of claim 52 wherein said two planes are substantially perpendicular to each other.

56. The tooth cleaning tool of claim 52 wherein the free ends of the bristles in each of the four rows lie along a corresponding smooth curve.

57. The tooth cleaning tool of claim 56 wherein said each of said corresponding smooth curves is convex relative to the elongated shaft.

58. The tooth cleaning tool of claim 45 wherein said elongated shaft and said plurality of bristles are integrally formed as a single unit.

59. The tooth cleaning tool of claim 45 wherein said elongated shaft is flexible.

60. The tooth cleaning tool of claim 59 wherein said elongated shaft and said plurality of bristles are injection molded as a single piece.

61. The tooth cleaning tool of claim 60 wherein said elongated shaft and said plurality of bristles are both made of plastic.

62. The tooth cleaning tool of claim 45 wherein the elongated shaft has a diameter of about 1 mm.

63. The tooth cleaning tool of claim 48 wherein the bristles within each of said rows are spaced approximately equally apart from each other.

64. The tooth cleaning tool of claim 48 wherein said plurality of bristles are all mounted on said elongated shaft along a region that is about 1 cm in length.

65. The tooth cleaning tool of claim 45 wherein each of the bristles of said plurality of bristles has a diameter of about 0.1 mm.

66. The tooth cleaning tool of claim 65 wherein the diameter of each of the bristles of said plurality of bristles decreases from the elongated shaft toward the free end of the bristle.

67. The tooth cleaning tool of claim 45 wherein each of the bristles of said plurality of bristles has a rounded tip.

68. An adapter for attachment to a hand held unit including a motor driven output shaft, said adapter comprising:
   a input member which during use couples to the motor driven output shaft of the hand held unit and is rotatable about a first axis;
   a rotatable output member to which a tooth cleaning tool is attached during use and which is rotatable about a second axis; and
   a transmission which transfers rotational movement of the input member about the first axis to the output member so that the output member has a rotational speed about the second axis that is different from the rotational speed of the input member.

69. The adapter of claim 68 wherein said transmission generates a lower rotational speed of the output member as compared to the input member.

70. The adapter of claim 69 wherein the transmission comprises a crown gear on an output side of the transmission and a pinion gear on an input side of the transmission, wherein said pinion gear meshes with the crown gear.

71. The attachment according to claim 24, wherein the bristles in each row are aligned at right angles to shaft.

* * * * *

UNITED STATES PATENT AND TRADEMARK OFFICE
CERTIFICATE OF CORRECTION

PATENT NO. : 6,253,404 B1  Page 1 of 1
DATED : July 3, 2001
INVENTOR(S) : Bernhard Boland and Michael Stolper It is certified that error appears in the above-identified patent and that said Letters Patent is hereby corrected as shown below:

<u>Title page,</u>
Item [56], U.S. PATENT DOCUMENTS, please add the following references:
-- 3,204,275    09/1965    Baker et al.
     5,000,684    03/1991    Odrich
     5,071,348    12/1991    Woog
     5,613,258    03/1997    Hilfinger et al. --

Item [56], FOREIGN PATENT DOCUMENTS, please add the following references:
--    93/05679    04/1993    WIPO --

Item [57], ABSTRACT,
Line 3, "hanle" should be -- handle --.

<u>Column 2,</u>
Line 51, "derive" should be -- drive --.

<u>Column 3,</u>
Line 49, "flexile" should be -- flexible --.

<u>Column 4,</u>
Line 3, "facilities" should be -- facilitates --.

<u>Column 11,</u>
Line 28, "handdle" should be -- handle --.

Signed and Sealed this

Fifteenth Day of October, 2002

*Attest:*

JAMES E. ROGAN
*Attesting Officer*    *Director of the United States Patent and Trademark Office*